US006862762B1

United States Patent
Johnson et al.

(10) Patent No.: US 6,862,762 B1
(45) Date of Patent: Mar. 8, 2005

(54) PATIENT SUPPORT APPARATUS

(75) Inventors: Michael Karl Johnson, Ellis, KS (US); Troy Dell Parson, Ellis, KS (US)

(73) Assignee: WLF, L.L.C., Kansas City, MO (US)

( * ) Notice: Subject to any disclaimer, the term of this patent is extended or adjusted under 35 U.S.C. 154(b) by 0 days.

(21) Appl. No.: 10/339,806

(22) Filed: Jan. 10, 2003

Related U.S. Application Data

(60) Provisional application No. 60/348,056, filed on Jan. 11, 2002, and provisional application No. 60/398,223, filed on Jul. 24, 2002.

(51) Int. Cl.[7] .......................... A61B 6/04; G03B 42/04; A61G 7/005; A61G 7/015
(52) U.S. Cl. .................. 5/601; 5/610; 5/618; 378/177; 378/181; 378/209
(58) Field of Search .................... 5/601, 600, 610, 5/613, 616, 617, 618; 378/177, 181, 209

(56) References Cited

U.S. PATENT DOCUMENTS

| | | | | |
|---|---|---|---|---|
| 1,557,662 A | * | 10/1925 | Crawford | 5/610 |
| 1,768,769 A | * | 7/1930 | Kelley | 378/155 |
| 2,295,006 A | * | 9/1942 | Philips | 5/610 |
| 2,337,395 A | * | 12/1943 | Leland, Jr. | 5/610 |
| 2,989,634 A | * | 6/1961 | Ould et al. | 378/177 |
| 3,149,349 A | * | 9/1964 | Nelson | 5/610 |
| 3,261,031 A | * | 7/1966 | Gates | 5/86.1 |
| 3,379,450 A | * | 4/1968 | Jones et al. | 280/657 |
| 3,406,772 A | * | 10/1968 | Ahrent et al. | 180/9.23 |
| 3,640,566 A | * | 2/1972 | Hodge | 297/68 |
| 3,826,922 A | * | 7/1974 | Ingles | 378/181 |
| 3,904,531 A | * | 9/1975 | Barrett et al. | 378/181 |
| 3,964,786 A | * | 6/1976 | Mashuda | 297/330 |
| 4,103,170 A | | 7/1978 | Spradlin | |
| 4,193,148 A | * | 3/1980 | Rush | 378/177 |
| 4,205,233 A | * | 5/1980 | Craig et al. | 378/209 |
| 4,407,543 A | * | 10/1983 | Mashuda | 297/330 |
| 4,557,471 A | * | 12/1985 | Pazzini | 5/618 |
| 4,559,655 A | | 12/1985 | Peck | |
| 4,637,652 A | * | 1/1987 | Bergenwall | 297/90 |
| 4,651,364 A | * | 3/1987 | Hayton et al. | 5/601 |
| 4,669,136 A | | 6/1987 | Waters et al. | |
| 4,905,266 A | * | 2/1990 | Kuck et al. | 378/177 |
| 4,916,725 A | * | 4/1990 | Quinter et al. | 378/177 |
| 5,023,967 A | * | 6/1991 | Ferrand | 5/607 |
| 5,072,463 A | * | 12/1991 | Willis | 5/618 |
| 5,127,705 A | * | 7/1992 | Antoine et al. | 297/68 |
| 5,138,729 A | * | 8/1992 | Ferrand | 5/713 |

(List continued on next page.)

FOREIGN PATENT DOCUMENTS

| | | | | |
|---|---|---|---|---|
| FR | 002523437 A | * | 9/1983 | A61G/7/00 |
| WO | WO093017649 A1 | * | 9/1993 | A61G/5/00 |

OTHER PUBLICATIONS

The Nelson Patient Handling Device Service Manual, Copyright 1991 W.H. McMills, Inc., 431 Waverly St., Pall Alto California, Front cover, pp. 2, 29–34 and back covers.

Primary Examiner—Robert G. Santos
(74) Attorney, Agent, or Firm—Spencer Fane Britt & Browne LLP

(57) ABSTRACT

The patient support apparatus includes a base frame and a patient support assembly. The patient support assembly is pivotably mounted the base frame and is moved by a first actuator to rotate between a horizontal position and an upright position. The patient support assembly includes an upper body portion, a lower body portion and a leg portion. The upper body portion, the lower body portion and the leg portion are pivotably interconnected with a linkage frame so that they can be moved in unison by a second actuator between a supine configuration and an upright, chair shaped configuration. Thus, the patient support apparatus is adjustable between a flat, bed shaped configuration and a seat shaped configuration and is also movable between a horizontal position and an upright position.

8 Claims, 8 Drawing Sheets

U.S. PATENT DOCUMENTS

| | | | |
|---|---|---|---|
| 5,155,758 A | | 10/1992 | Vogl |
| 5,222,115 A | * | 6/1993 | Highgenboten ............. 378/177 |
| 5,345,629 A | * | 9/1994 | Ferrand ......................... 5/710 |
| 5,356,172 A | * | 10/1994 | Levy et al. ................. 280/650 |
| 5,366,036 A | | 11/1994 | Perry |
| 5,422,928 A | * | 6/1995 | Payne ........................ 378/177 |
| 5,454,126 A | | 10/1995 | Foster et al. |
| 5,537,700 A | | 7/1996 | Way et al. |
| 5,544,376 A | | 8/1996 | Fromson |
| 5,703,925 A | * | 12/1997 | Wright ....................... 378/181 |
| 5,724,685 A | | 3/1998 | Weismiller et al. |
| 5,737,786 A | | 4/1998 | Yamamoto |
| 5,740,568 A | | 4/1998 | Elliott |
| 5,996,149 A | * | 12/1999 | Heimbrock et al. ........... 5/601 |
| 6,058,533 A | | 5/2000 | Nelson |
| 6,151,732 A | * | 11/2000 | Heimbrock et al. ........... 5/601 |
| 6,243,897 B1 | * | 6/2001 | Sumiya ........................ 5/610 |
| 6,341,398 B1 | * | 1/2002 | Heimbrock et al. ........... 5/601 |
| 6,722,783 B2 | * | 4/2004 | Jackson, Sr. ................ 378/178 |

* cited by examiner

PATIENT SUPPORT APPARATUS

CROSS REFERENCES TO RELATED APPLICATIONS

This application claims the benefit of U.S. Provisional Patent Application No. 60/348,056 filed Jan. 11, 2002 and U.S. Provisional Patent Application No No. 60/398,223 filed Jul. 24, 2002.

FIELD OF THE INVENTION

This invention relates to an articulated patient support apparatus having a first function for, moving patient supporting surfaces between a first flat configuration and a second chair shaped configuration and a second function for moving the patient supporting surfaces between a first horizontal position and a second upright position.

BACKGROUND OF THE INVENTION

Hospitals and other care facilities use items of equipment to move and support patients. Typically, such items of equipment tend to be specialized items of equipment including hospital beds, wheelchairs, gurneys and operating tables.

Hospitals and other care facilities occasionally have a need to support and move "bariatric" patients having body weights in excess of 300 lbs. It may be cost efficient for a hospital or care facility to procure an array of specialized equipment such as beds, wheelchairs, gurneys and operating tables to support or move non-bariatric patients. It is too costly to procure an array of specialized items of equipment to accommodate a small number of bariatric patients. However, it is cost efficient for an institution to obtain a very small number of multi-functional items of equipment to accommodate the relatively rare bariatric patient. Since bariatric patients and their care givers can be injured when a bariatric patient is moved between specialized items of equipment, it is advantageous to employ one multi-functional item of equipment so that there is no need to move a bariatric patient between specialized items of equipment. Therefore, it would be advantageous to have a multi-functional item of equipment capable of supporting bariatric patients that can function as a gurney, a bed, a wheelchair, an operating table and an x-ray table and which can also transition between performing these various functions without removing the patient from the item of equipment. Care givers can also sustain injuries while helping a bariatric patient to stand. Accordingly, what is also needed is a multi-functional item of equipment that can tilt a bariatric patient into a standing position as well as perform all of the above described functions.

SUMMARY OF THE INVENTION

Accordingly, an object of the present invention is to provide a multi-functional patient support apparatus that can support and move a bariatric patient. Another object of the present invention is to provide a multi-functional apparatus that can transition a patient between a flat position in which the patient is lying down and a sitting position and which can also transition a patient between a flat position in which the patient is lying down and a standing position. Still another object of the present invention is to provide an apparatus that is powered by actuators to move between the various above described positions so that such movements can be assisted by a care giver with very little physical effort. Yet, still another object of the present invention is to provide an item of equipment that can adapted to accommodate bariatric patients and that can function as a wheelchair, a bed, a gurney, an operating table and a rehabilitation apparatus capable of moving a patient into a standing position. And yet another object of the present invention is to provide an apparatus that can be used as an upright or horizontal x-ray table.

These and other objects of the invention are attained in a patient support and transport apparatus that is able to support and transport a bariatric patient while the patient is in various positions including a supine, or lying down position and a seated position and that is able to reposition a patient continuously through intermediate positions between the supine position and the seated position and between the supine position and the standing position. The patient support apparatus includes a base frame and a patient support assembly. The patient support assembly is pivotably mounted to the base frame so that the patient support assembly can rotate about a first axis between a horizontal position and an upright position. A first actuator couples the patient support assembly to the base frame so that when the first actuator extends, the patient support assembly rotates about the first axis between the horizontal position and the upright, standing position. The first actuator is also mounted to the base frame such that the fully extended first actuator may be manually translated in relation to the base frame so that the patient support assembly can be manually moved between the upright position to the horizontal position.

The patient support assembly includes a linkage frame, a lower body portion for supporting the upper legs and buttocks, a leg portion for supporting the lower legs and an upper body portion for supporting the upper body above the waist. The linkage frame is pivotably mounted to the base frame. The lower body portion is disposed in a parallel fashion generally above the linkage frame. The leg portion pivotably connects to the linkage frame and to the lower body portion. The upper body portion pivotably connects to the lower body portion and to the linkage frame. Accordingly, the linkage frame, the lower body portion, the leg portion and the upper body portion of the patient support assembly are interconnected such that when one of the portions is moved relative to a connecting portion, the entire assembly moves between a chair shaped configuration an a flat, bed shaped configuration. The leg portion is coupled by a second actuator to the linkage frame. When the second actuator extends, the leg portion rotates up, the lower body portion translates relative to the linkage frame toward the head end and the upper body portion rotates down until the leg portion, the lower body portion and the upper body portion present a substantially flat surface. When the second actuator contracts, the leg portion rotates down, the lower body portion translates toward the foot end and the upper body portion rotates up until the leg portion, the lower body portion and the upper body portion present an upright chair shaped configuration.

The upper body portion and the lower body portion have patient supporting panels that are transparent to x-rays. The patient support assembly carries an x-ray cartridge carriage that can be used to position an x-ray cartridge under the lower body and the upper body of the patient. The patient support assembly has provisions for mounting surgical equipment, so that the patient support apparatus can also be used as an operating table. The patient support assembly also has provisions for mounting side rails.

Thus, the patient support apparatus of the present invention has two basic modes of movement. In a first mode of movement, the patient support assembly rotates relative to the base frame so that a patient in a horizontal position may be raised to an upright, standing position. A patient who has been lifted to an upright position can easily step off from the apparatus and begin walking. In a second mode, a patient supported by the apparatus may be supported in a flat, supine position and an upright, sitting position or any position between those two positions. Because actuators are employed to move the various components of the apparatus, they can be programmed to operate in a number of pre-selected sequences by a control module having pre-selected sequences of operations. Moreover, because the patient support apparatus supports x-ray procedures as well as surgery, the patient support apparatus can be used to meet a wide range of therapeutic needs.

BRIEF DESCRIPTION OF THE DRAWINGS

The invention may be best understood by those having ordinary skill in the art by reference to the following detailed description when considered in conjunction with the accompanying drawing in which.

DETAILED DESCRIPTION OF THE INVENTION

Figure 1:
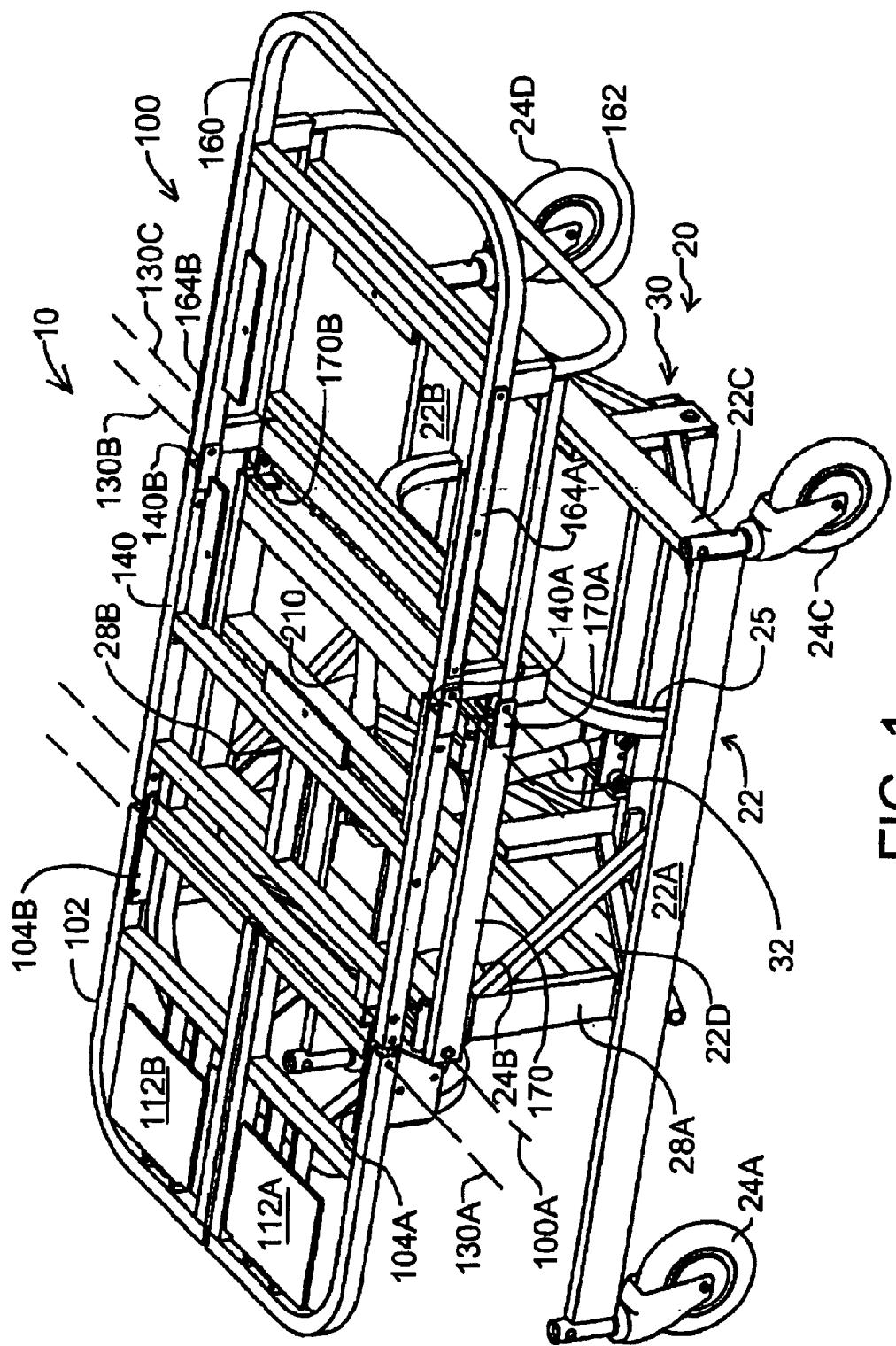
FIG. 1 is a perspective view of the patient support apparatus.

Turning now to the drawings, wherein like reference numerals identify identical or corresponding elements, and more particularly to FIG. 1 thereof, a patient support apparatus 10 is shown having a base frame 20 and a patient support assembly 100.

Figure 2:
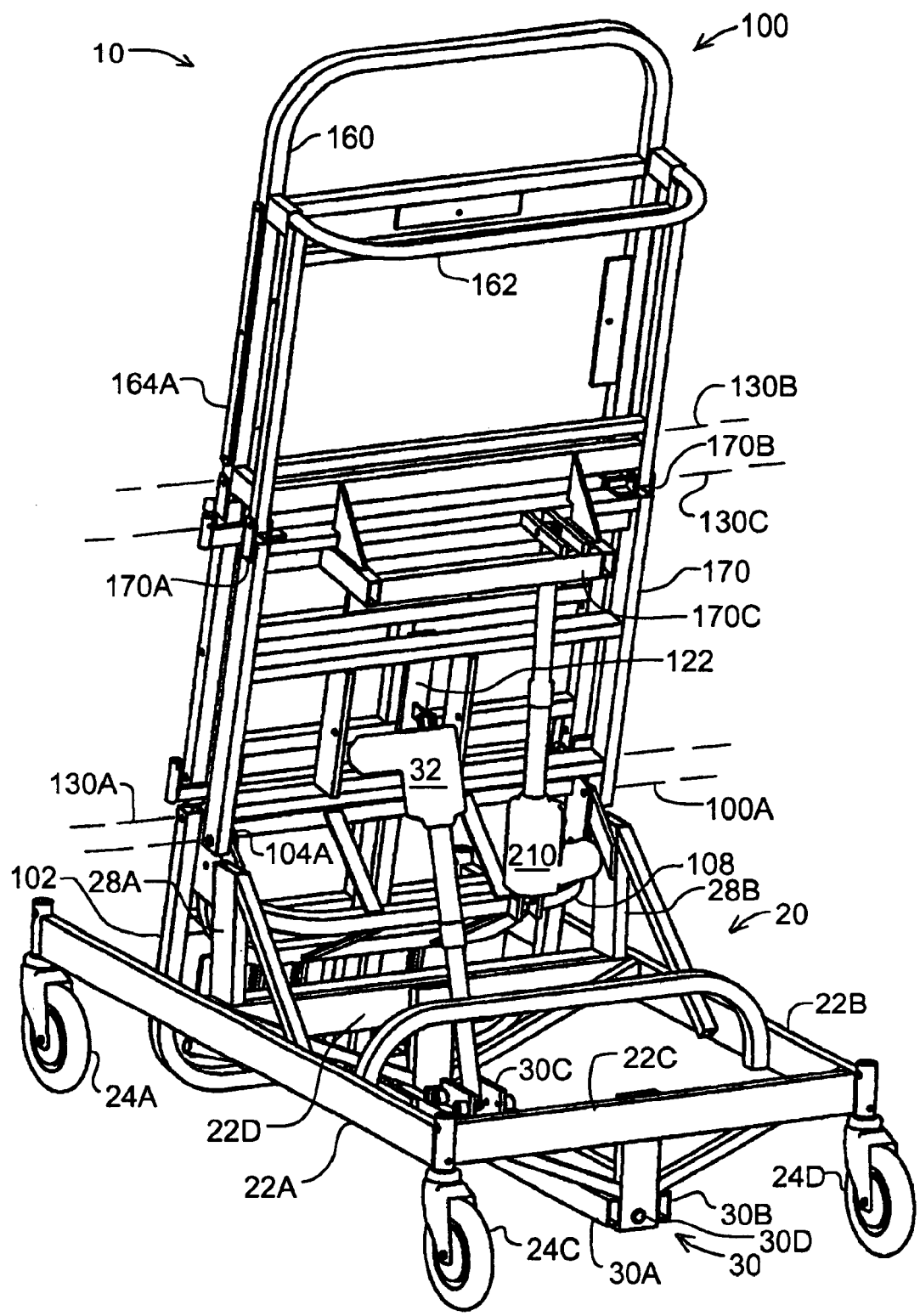
FIG. 2 is a perspective view of the patient support apparatus with the patient support assembly in an upright position.

As shown in FIGS. 1 and 2, base frame 20 includes a horizontal rectangular carriage 22, upright members 28A and 28B, a support member 25 and an actuator support structure 30. Rectangular carriage 22 is a rigid structure including two side members 22A and 22B, an end member 22C and a transverse member 22D. Carriage 22 is supported by wheel assemblies 24A, 24B, 24C and 24D. Wheel assembly 24C and 24D are caster wheels that allow carriage 22 to turn. Upright members 28A and 28B are fixed to side members 22A and 22B. At the top end of upright members 28A and 28B are bearings for receiving pins (not shown) which are common to patient support assembly 100. Support member 25 arches between side members 22A and 22B and provides a second support for patient support assembly 100 when patient support assembly 100 is in a horizontal position as shown in FIGS. 1 and 3.

Figure 3:
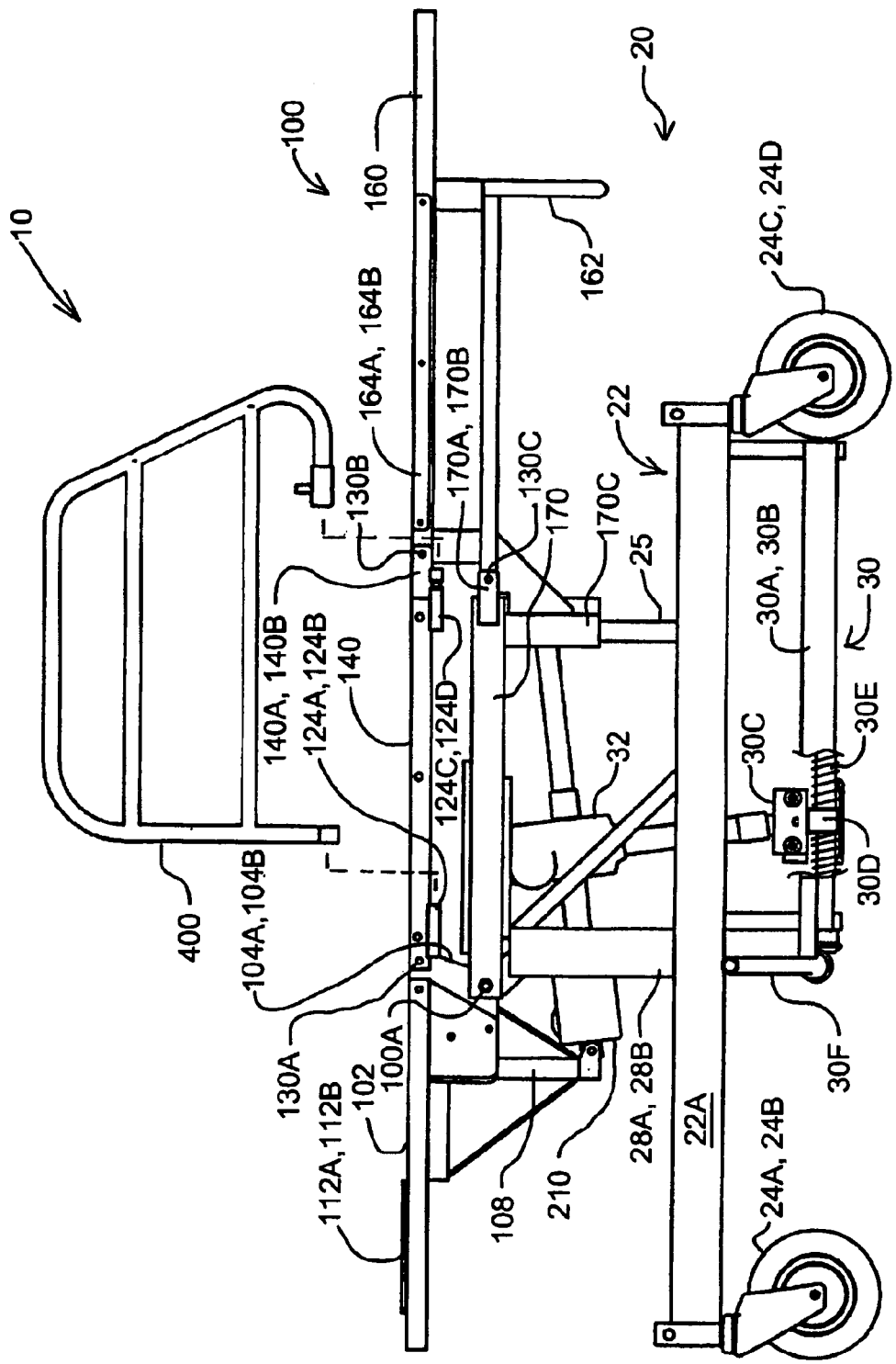
FIG. 3 is a side view of the patient support apparatus.
Figure 4:
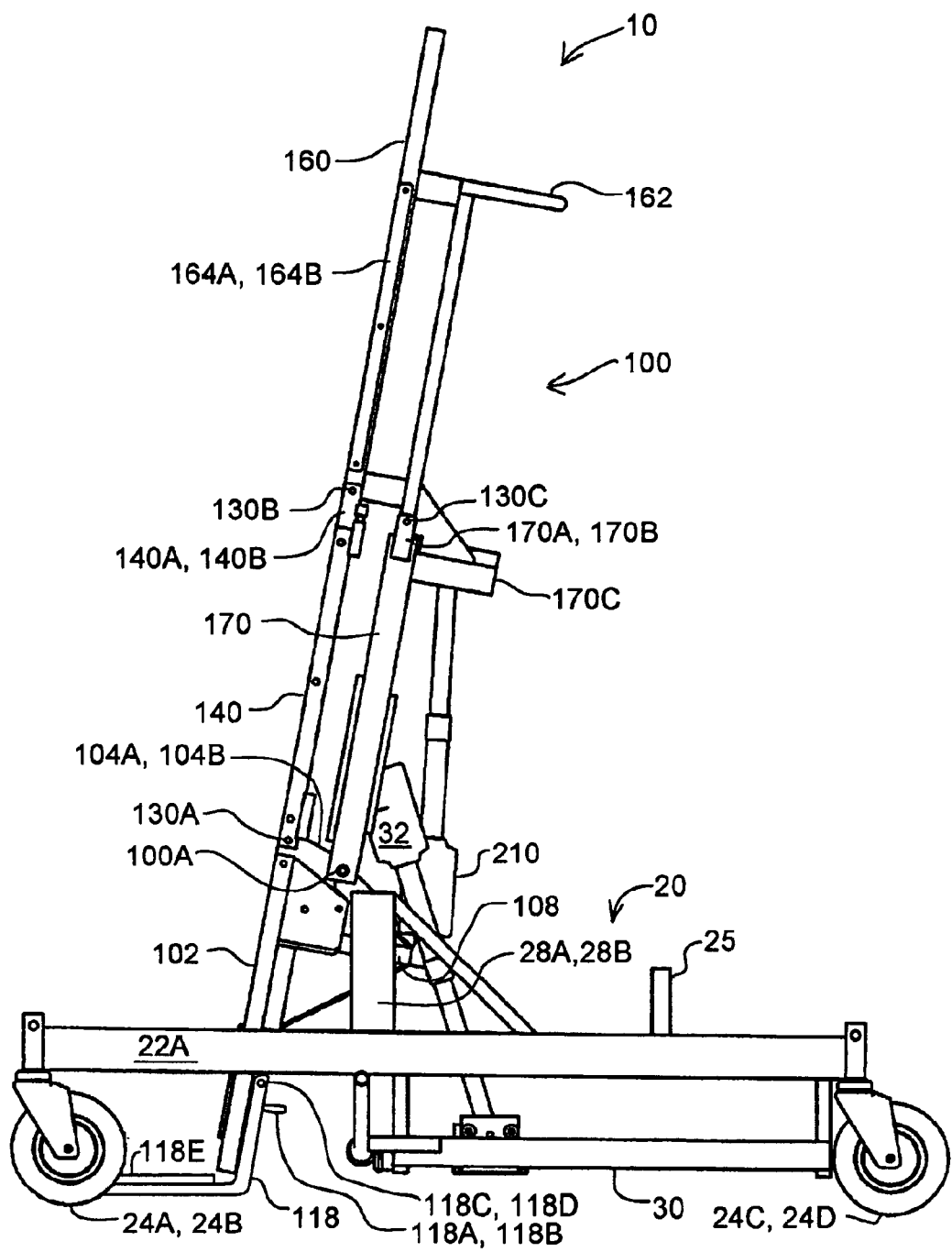
FIG. 4 is a top view of the patient support apparatus.

Patient support assembly 100 can be rotated about a first axis 100A between a first substantially horizontal position for supporting a patient in a supine position as shown in FIGS. 1 and 3 and a second upright position shown in FIGS. 2 and 4 for supporting a patient in a substantially standing position. As is noted above, bearings at the upper ends of upright members 28A and 28B receive pins that are common to patient support assembly 100. In particular, a linkage frame 170 which is a part of patient support assembly 100 is pinned to base frame 20 at the bearings located near the upper ends of upright members 28A and 28B. As can be seen in FIG. 2, first actuator 32 is pivotably mounted to both actuator support structure 30 and a brace 122 that spans linkage frame 170 of patient support assembly 100. When first actuator 32 extends or retracts, patient support assembly 100 rotates around first axis 100A between a horizontal position as shown in FIG. 3 and an upright position as shown in FIG. 4. The actuator arrangement described here is only one of many equivalent arrangements that could be selected for rotating patient support assembly 100 relative to base frame 20.

First actuator 32 is mounted to actuator support structure 30 so that it can translate along actuator support structure 30 such that when first actuator 32 is fully extended, patient support assembly 100 can be pivoted to a horizontal position by translating the base of actuator 32. Support structure 30 includes a pair of actuator support members 30A and 30B which extend between end member 22C and transverse member 22D of carriage 22. First actuator 32 is mounted to actuator support structure 30 by an actuator truck 30C which has rollers that engage support members 30A and 30B such that actuator truck 30C can move along the lengths of support members 30A and 30B between end member 22C and transverse member 22D. As is shown in FIG. 3, actuator truck 30C is secured by an internally threaded dog 30D to a correspondingly threaded actuator bar 30E that is rotatably mounted between support members 30A and 30B. Actuator truck 30C and threaded actuator bar 30E are normally stationary. When threaded actuator bar 30E is turned upon its axis by a crank 30F, actuator truck 30C is moved along support rails 30A and 30B. This arrangement provides an alternate means for raising and lowering patient support assembly 100 even if first actuator 32 is not operating.

Figure 5:
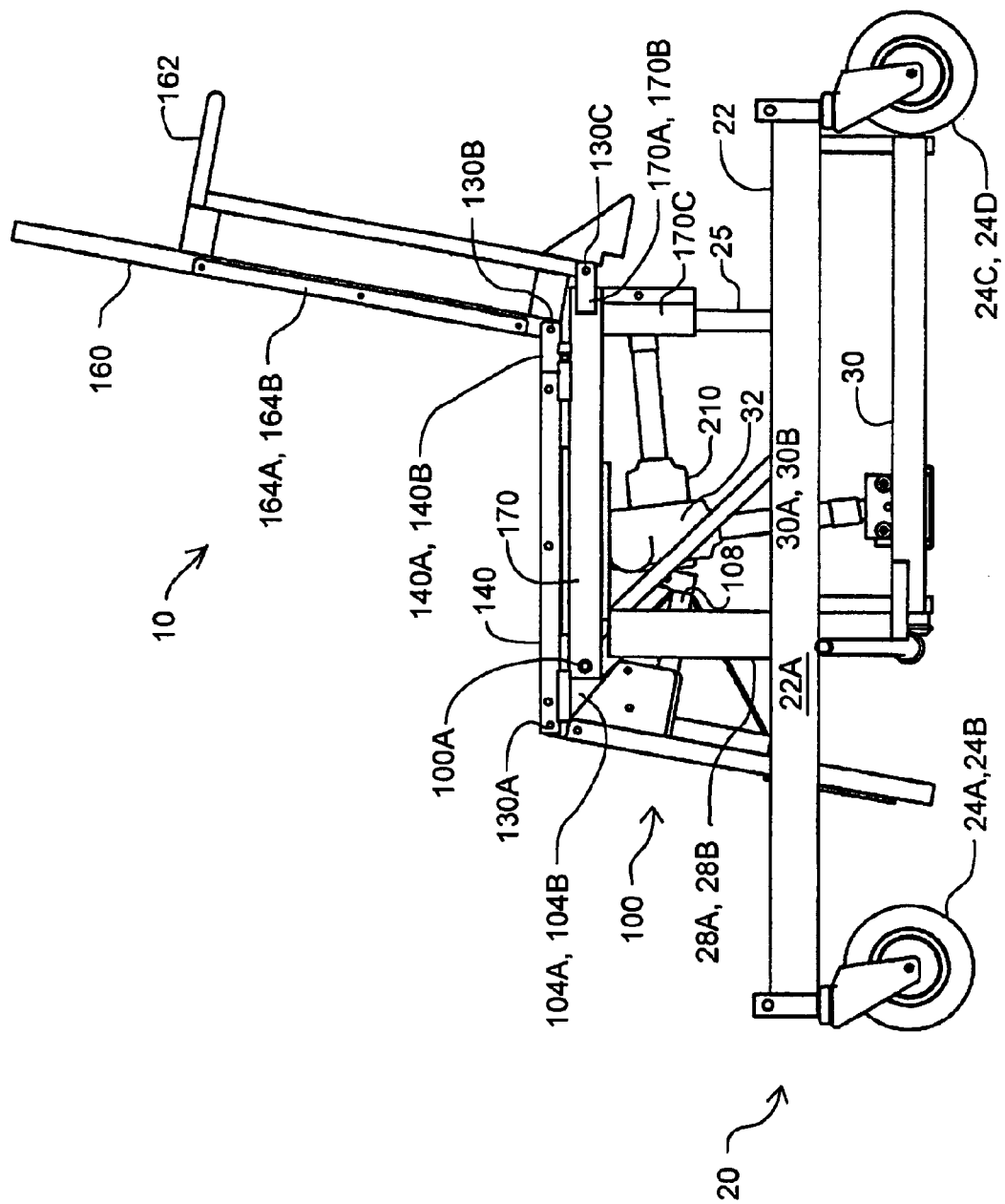
FIG. 5 is a side view of the patient support apparatus showing the patient support assembly articulated in a seat shaped configuration.
Figure 6:
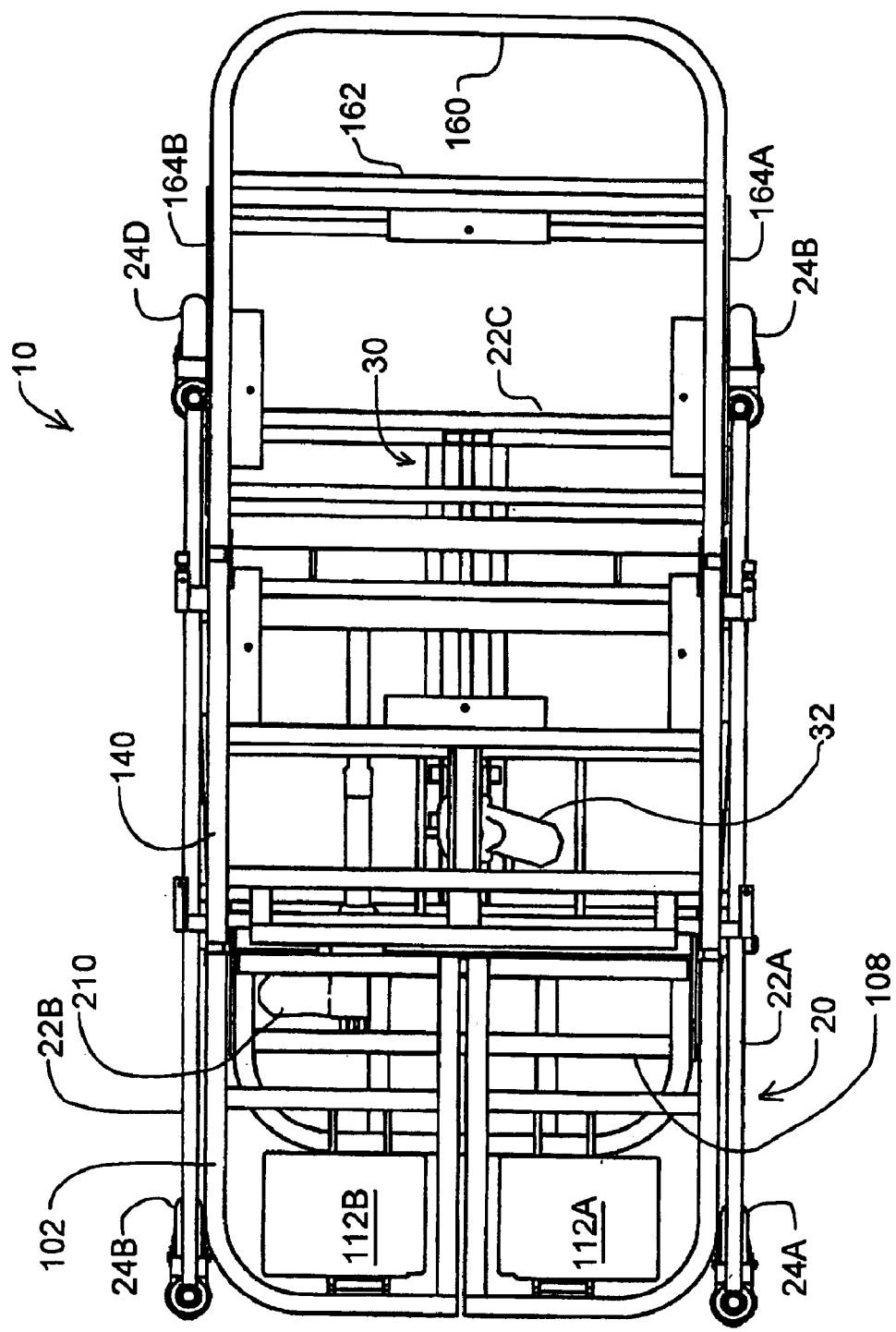
FIG. 6 is a side view of the patient support apparatus showing the patient support assembly in an upright position.

Patient support assembly 100 is an articulated structure for supporting a patient in a range of positions between the first substantially horizontal position for supporting a patient in a supine position as shown in FIGS. 1 and 3 and a third chair shaped position for supporting a patient in a seated position as shown in FIG. 5. For ease of illustration, patient support assembly 100 is shown in FIGS. 1, 2 and 6 without coverings and panels. Such coverings and panels would ordinarily provide surfaces for supporting a mattress or a pad. Patient support assembly 100 includes four basic portions which are linked together in an articulated structure: (1) a leg portion 102 for supporting the lower legs of a patient, (2) a lower body portion 140 for supporting the upper legs and hips of a patient, (3) an upper body portion 160 for supporting the upper body portion of a patient above the hips of the patient and (4) a linkage frame 170 which is positioned parallel to lower body portion 140 and which pivotably connects between leg portion 102 and upper body portion 160.

Leg portion 102, linkage frame 170, lower body portion 140 and upper body portion 160 of patient support assembly 100 are connected to each other so that they can pivot relative to each other about four axis: (1) first axis 100A which is an axis of rotation between leg portion 102 linkage frame 170 (as well as the axis of rotation between patient support assembly 100 and base frame 20 as described above), (2) a second axis 130A which is an axis of rotation between leg portion 102 and lower body portion 140, (3) a third axis 130B which is an axis of rotation between upper body portion 160 and lower body portion 140 and (4) a fourth axis 130C which is an axis of rotation between upper body portion 160 and linkage frame 170.

Leg portion 102 includes opposite identical fittings 104A and 104B. Fittings 104A and 104B are joined with linkage frame 170 such that they can pivot about first axis 100A. Fittings 104A and 104B are also joined with lower body portion 140A such that they can pivot about axis 130A. Linkage frame 170 has a pair of devises 170A and 170B that receive members that extend from upper body portion 160. In the same way, lower body portion 140 has a pair of clevises 140A and 140B that receive members extending from upper body support frame 160. Leg portion 102 also includes an actuator brace 108 for receiving the proximate end of a second actuator 210. The distal end of second actuator 210 is connected to an actuator brace 170C which is fixed to linkage frame 170.

The relative movements of the portions of body support assembly 100 can best be seen by referring to FIG. 3 and FIG. 5. As seen from the vantage point of FIG. 3, when second actuator 210 contracts, leg portion 102 rotates counter clockwise about first axis 100A as it pulls lower body portion 140 causing it to translate to the left which in turn pulls upper body portion 160 to cause it to rotate counter clockwise about fourth axis 130C until leg portion 102, lower body portion 140 and upper body portion 160 present a chair shaped configuration as shown in FIG. 5. As seen from the vantage point of FIG. 5, when second actuator 210 extends, leg portion 102 rotates clockwise about first axis 100A as it pushes lower body portion 140 to translate to the right as it in turn pushes upon upper body portion 160 so that upper body portion 160 rotates clockwise about fourth axis 130C until leg portion 102, lower body portion 140 and upper body portion 160 present a substantially flat upper surface as shown in FIG. 3. It should be understood that while leg portion 102 can pivot with respect to linkage frame 170 around first axis 100A as shown and described above, it would also be possible to pivot leg portion 102 about a second axis which is stationary with respect to linkage frame 170 and which is also parallel to first axis 100A. It should also be understood that although second actuator 210, in this preferred embodiment is shown connecting linkage frame 170 and leg portion 102, a second actuator could also be devised to connect linkage frame 170 and one of the other portions of patient support assembly 100 in order to accomplish the same function as actuator 210.

As can be understood from the above description, patient support apparatus 10 operates in two basic modes. In the first mode, by operation of first actuator 32, a patient who is lying down can be raised into an upright position. The first mode of operation makes it possible for a patient who can not raise himself or herself up but who can stand and walk, to be raised to an upright position for exercise and rehabilitation. In the second mode, by operation of second actuator 210, the components of patient support assembly 100 can be arranged within a range of configurations between a flat configuration and a chair shaped configuration. When operating in the second mode, linkage frame 170 of patient support assembly 100 should be down and resting upon support member 25 of base frame 20. Because base frame 20 is supported by wheels, it is possible to transport a patient as with a gurney in a supine position or as with a wheelchair in a sitting position. A rail 162 fixed to the back of upper body portion 160 provides a hand grip for a care giver to push and maneuver patient support apparatus 10 particularly when patient support assembly 100 is arranged in the chair position. With the addition of a control unit for controlling the first and second actuators, it is possible to have preprogrammed sequences of movement so that a patient may be moved through sequences of positions between positions in which the patient is lying down, sitting and standing upright.

Figure 7:
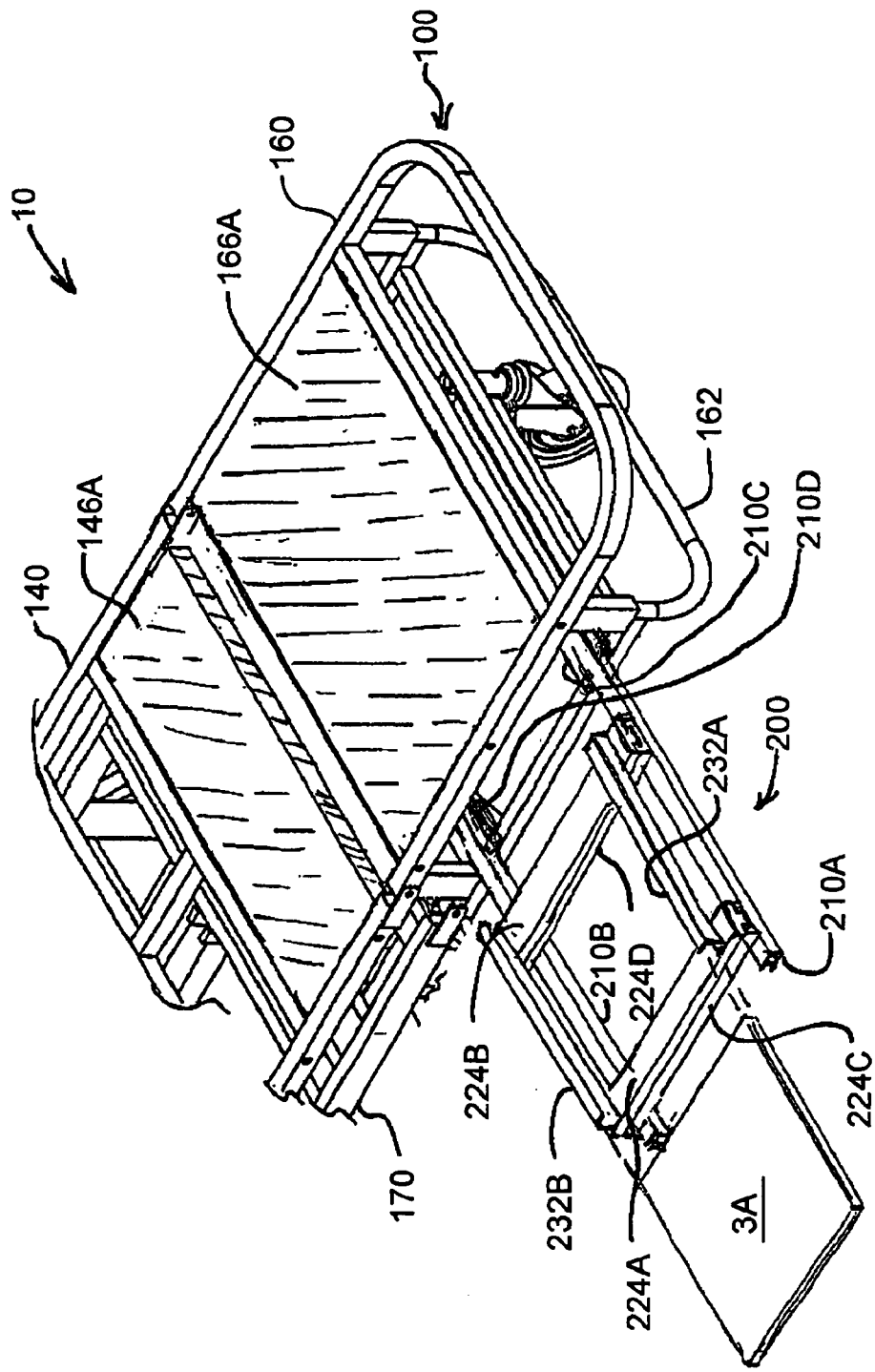
FIG. 7 is a perspective view of the patient support apparatus showing an extended X-Ray Cartridge support rack.

FIG. 7 illustrates an X-Ray carriage 200 and x-ray transparent patient support panels 146A and 166A which are important features of patient support apparatus 10. X-ray transparent patient support panel 146A mounted to lower body portion 140 and x-ray transparent patient support panel 166A mounted to upper body portion 160 are fashioned from a material such as phenolic that is transparent to X-rays. X-ray transparent patient support panels 146A and 166A make it possible to X-ray any portion of a large extent of the body of a patient supported by patient support apparatus 10. X-ray carriage 200 is a positioning member for moving an X-ray cartridge from side to side between an extended position and a retracted position and up and down between an upper position and a lower position thus making it possible to obtain X-ray images over a large portion of a patient's body. X-ray carriage 200 is mounted to upper body portion 160 of patient support assembly 100. X-ray carriage 200 includes transverse rails 210A and 210B, longitudinal rails 224A and 224B and cartridge rails 232A and 232B adapted for receiving an x-ray cartridge 3A. Transverse rails 210A and 210B slide between an extended position shown in FIG. 7 and a retracted position inside upper body portion 160. Transverse rails 210A and 210B slide along transverse tracks 210C and 210D which are fixed to the bottom part of upper body frame 160. In a similar fashion, longitudinal rails 224A and 224B are slidably mounted to transverse rails 210A and 210B by a pair of longitudinal tracks 224C and 224D that are fixed to transverse rails 210A and 210B. When transverse rails 210A and 210B are retracted inside upper body frame 160, longitudinal rails 224A and 224B can move upon longitudinal tracks 224C and 224D in unison between a first upper position in which X-ray plate 3A is under x-ray panel 166A to a second lower position where x-ray cartridge 3A is under x-ray panel 146A. When an X-ray cartridge is secured by cartridge rails 232A and 232B, it can be translated under X-ray panels 166A and 146A upon transverse rails 210A and 210B and longitudinal rails 224A and 224B so that large portions of a supported patient's body can be x-rayed.

Because it is possible to rotate patient support assembly 100 into an upright position as described above, x-ray images of a patient can be obtained while the patient is in an upright position. This is an important capability for patient support apparatus 10 since x-rays of a patient are often taken in an upright position shortly after a surgery where the digestive system of bariatric patient has been altered to facilitate weight loss.

A can be seen in FIG. 3, patient support assembly 100 also includes a set of rail fittings 124A, 124B, 124C and 124D mounted to either side of lower body portion 140. As can be seen in FIG. 3, rail fittings 124A, 124B, 124C and 124D are configured to receive a pair of bed rails 400.

Leg portion 102 also includes a pair of folding foot support panels 112A and 112B which rotate out into a position for supporting a patient's feet as shown in FIG. 5. Foot support panels 112A and 112B can also be mounted to leg portion 102 so that they can be translated longitudinally relative to leg portion 102 to accommodate patients of varying height.

FIG. 4 shows that a foot plate assembly 118 can be mounted to leg portion 102. The purpose of foot plate assembly 118 is to provide a support for a patient when he or she is being tilted into an upright position. Foot plate assembly 118 includes a frame that is pivotably mounted to leg portion 102 on joints 118C and 118D located on opposite sides of leg portion 102 and a foot plate 118E that extends across the lower end of leg portion 102. Foot plate 118 can be pinned in the extended position by pins 118A and 118B as shown in FIG. 4 or can be pinned in a retracted position by pins 118A and 118B when it is swung behind leg portion 102.

Figure 8:
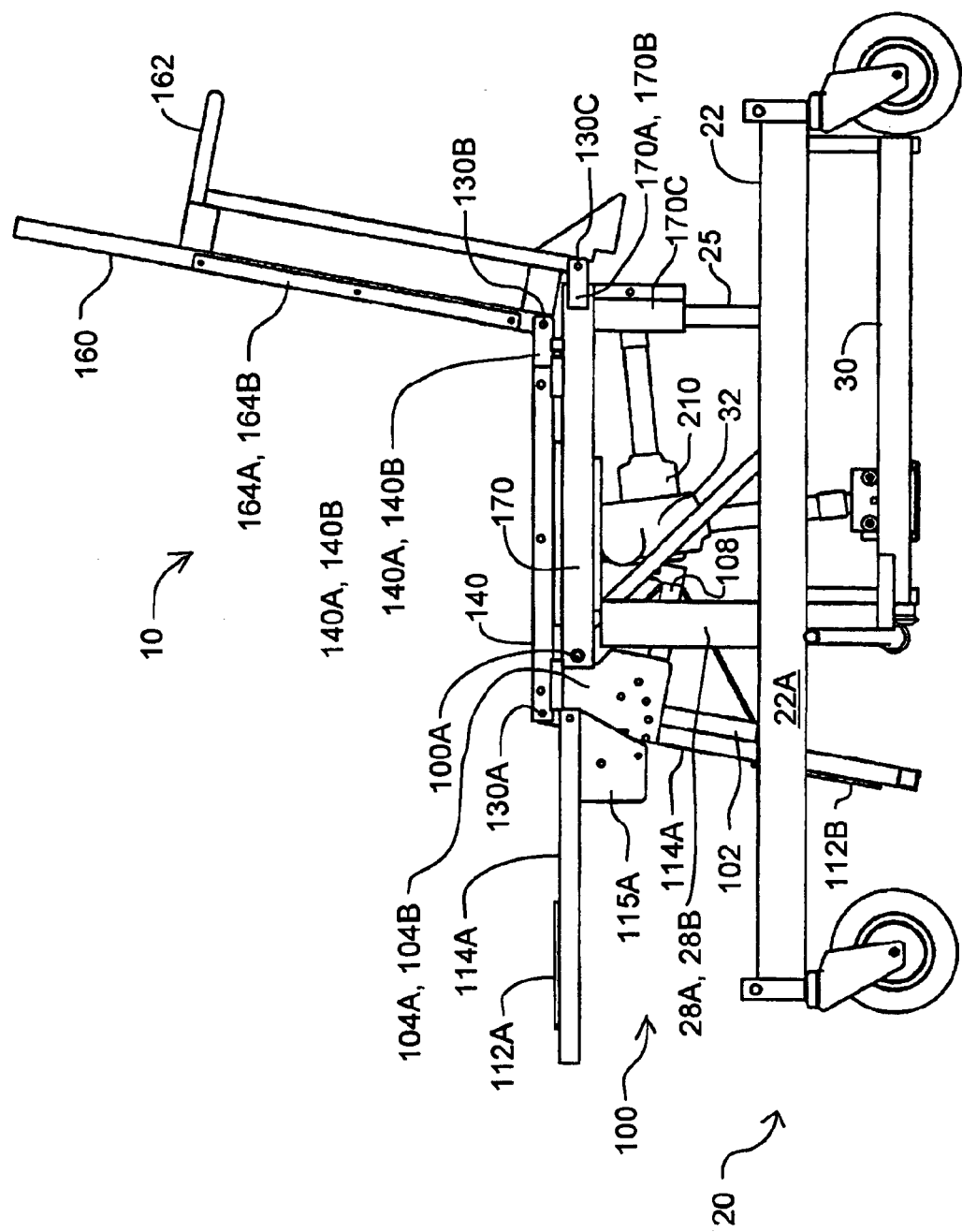
FIG. 8 is a side view of the patient support apparatus showing the patient support assembly articulated in a seat shaped configuration with one leg support assembly in a raised position.

As can be best seen in FIG. 8, leg portion 102 may include separate leg support assemblies 114A and 114B that can be separately, pinned in one of a series of positions. Each leg support assembly 114A and 114B is pivotably mounted by fitting 115A and 115B to leg portion fittings 104A and 104B located on opposite sides of leg portion 102. As can be seen in FIG. 8, a corresponding pattern of holes is provided in leg portion fittings 104A and 104B and fittings 115A and 115B so that each leg support assembly may be arranged in one of a series of positions ranging from a retracted position as shown for leg support assembly 114B in FIG. 8 to an extended position as shown for leg support assembly 114A in FIG. 8.

As can be best seen in FIGS. 1 and 2, patient support apparatus 10 includes clamp members 164A and 164B mounted on either side of upper body portion 160. These clamp members make it possible to mount various items of equipment used in surgery so that patient support apparatus 10 can also be used as an operating table.

Accordingly, the patient support apparatus described above provides a means for supporting and transporting patients in a large range of therapeutic situations. The patient support apparatus meets a primary objective of the invention by providing an apparatus structural system that that is able to support and transport a bariatric patient while the patient is in various positions including a lying down position and a seated position and that is able to reposition a patient continuously through intermediate positions between the lying down position and the seated position and between the lying down position and an upright position. The patient support apparatus described above meets an another object of this invention by providing an apparatus that can be used transport a patient while in the above described positions including the lying down position and the seated positions. The patient support apparatus described above meets yet another object of the present invention by providing a patient support apparatus that can be used raise a patient from a lying down position to a standing position so that the patient may walk and otherwise perform rehabilitating exercises without having to first lift himself or herself into a standing position or without having to be lifted into a standing position by care givers. And finally, the patient support apparatus described above meets yet another object of the present invention by providing a patient support apparatus having an X-ray carriage and x-ray panels so that a patient can be x-rayed when in a flat position between a lying down position or an upright position.

Numerous modifications and variations of this preferred embodiment may occur to those skilled in the art in light of this disclosure. Accordingly, it is expressly to be understood that these modifications and variations, and equivalents thereof, shall be considered to be within the spirit and scope of the invention as defined in following claims.

Having thus described the invention, what is claimed as new and desired to be secured by Letters Patent is:

1. An apparatus for supporting a patient, comprising;
(a) a base frame,
(b) a patient support assembly pivotably mounted to the base frame for movement between a first substantially horizontal position for supporting a patient in a supine position and a second substantially upright position for supporting a patient in a substantially standing position,
(c) an actuator connecting the base frame and the patient support assembly and operable between a retracted position and an extended position for moving the patient support assembly between the first substantially horizontal position and the second substantially upright position,
(d) the patient support assembly including a lower body portion, a leg portion pivotably mounted at one end of the lower body portion and an upper body portion pivotably mounted at the opposite end of the lower body portion, the portions adjustable between the first substantially horizontal position and a third chair shaped position for supporting a patient in a seated position, wherein the patient support assembly includes an X-ray transparent patient support and an X-ray cartridge carriage behind the X-ray transparent patient support for X-ray imaging of a patient, the X-ray cartridge carriage including a positioning member for movement between an extended position and a retracted position and for movement between an upper position and a lower position.

2. An apparatus for supporting a patient, comprising;
(a) a base frame,
(b) a patient support assembly pivotably mounted to the base frame for movement between a first substantially horizontal position for supporting a patient in a supine position and a second substantially upright position for supporting a patient in a substantially standing position,
(c) an actuator connecting the base frame and the patient support assembly and operable between a retracted position and an extended position for moving the patient support assembly between the first substantially horizontal position and the second substantially upright position,
(d) the patient support assembly including a lower body portion, a leg portion pivotably mounted at one end of the lower body portion and an upper body portion pivotably mounted at the opposite end of the lower body portion, the portions adjustable between the first substantially horizontal position and a third chair shaped position for supporting a patient in a seated position, the portions of the patient support assembly include X-ray transparent patient support panels, and the patient support assembly also includes an X-ray carriage for receiving and positioning an X-ray cartridge behind the X-ray transparent patient support panels opposite a patient, the X-ray carriage including transverse tracks fixed to the patient support assembly, transverse rails slidably mounted to the transverse tracks for translation between an extended position and a retracted position, longitudinal tracks fixed to the transverse rails and longitudinal rails slidably mounted to the longitudinal tracks for translation between an upper position and a lower position, the longitudinal rails adapted to slidably receive an X-ray cartridge whereby the X-ray cartridge may be moved between the extended position and the retracted position and positioned between the upper position and the lower position.

3. An apparatus for supporting a patient, comprising;

(a) a base frame, (b) a patient support assembly pivotably mounted to the base frame for movement between a first substantially horizontal position for supporting a patient in a supine position and a second substantially upright position for supporting a patient in a substantially standing position, (c) a first actuator connecting the base frame and the patient support assembly, the first actuator operable between a retracted position and an extended position for moving the patient support assembly between the first position and the second position, wherein the first actuator is mounted to the base frame by a movable truck such that when the first actuator is in the extended position, the truck may be translated relative to the base frame to cause the patient support assembly to move between the second position and the first position, (d) the patient support assembly including a lower body portion, a leg portion pivotably mounted at one end of the lower body portion, an upper body portion pivotably mounted at the opposite end of the lower body portion and a linkage frame pivotably connecting the leg portion and the upper body portion, the portions adjustable between the first substantially horizontal position and a third chair shaped position for supporting a patient in a seated position, (e) a second actuator coupling the linkage frame of the patient support assembly to one other portion of the patient support assembly, the second actuator for moving the portions of the patient support assembly between the first position and the third position.

4. An apparatus for supporting a patient, comprising;

(a) a base frame, (b) a patient support assembly pivotably mounted to the base frame for movement between a first substantially horizontal position for supporting a patient in a supine position and a second substantially upright position for supporting a patient in a substantially standing position, wherein the patient support assembly includes an X-ray transparent patient support and an X-ray cartridge carriage behind the X-ray transparent patient support for X-ray imaging of a patient, the X-ray cartridge carrier including a positioning member for movement between an extended position and a retracted position and for movement between an upper position and a lower position, (c) a first actuator connecting the base frame and the patient support assembly, the first actuator operable between a retracted position and an extended position for moving the patient support assembly between the first position and the second position, (d) the patient support assembly including a lower body portion, a leg portion pivotably mounted at one end of the lower body portion, an upper body portion pivotably mounted at the opposite end of the lower body portion and a linkage frame pivotably connecting the leg portion and the upper body portion, the portions adjustable between the first substantially horizontal position and a third chair shaped position for supporting a patient in a seated position, (e) a second actuator coupling the linkage frame of the patient support assembly to one other portion of the patient support assembly, the second actuator for moving the portions of the patient support assembly between the first position and the third position.

5. An apparatus for supporting a patient, comprising;

(a) a base frame, (b) a patient support assembly pivotably mounted to the base frame for movement between a first substantially horizontal position for supporting a patient in a supine position and a second substantially upright position for supporting a patient in a substantially standing position, (c) a first actuator connecting the base frame and the patient support assembly, the first actuator operable between a retracted position and an extended position for moving the patient support assembly between the first position and the second position, (d) the patient support assembly including a lower body portion, a leg portion pivotably mounted at one end of the lower body portion, an upper body portion pivotably mounted at the opposite end of the lower body portion and a linkage frame pivotably connecting the leg portion and the upper body portion, the portions adjustable between the first substantially horizontal position and a third chair shaped position for supporting a patient in a seated position, the portions of the patient support assembly include X-ray transparent patient support panels, and the patient support assembly also includes an X-ray carriage for receiving and positioning an X-ray cartridge behind the X-ray transparent patient support panels opposite a patient, the X-ray carriage including transverse tracks fixed to the patient support assembly, transverse rails slidably mounted to the transverse tracks for translation between an extended position and a retracted position, longitudinal tracks fixed to the transverse rails and longitudinal rails slidably mounted to the longitudinal tracks for translation between an upper position and a lower position, the longitudinal rails adapted to slidably receive an X-ray cartridge whereby the X-ray cartridge may be moved between the extended position and the retracted position and positioned between the upper position and the lower position, (e) a second actuator coupling the linkage frame of the patient support assembly to one other portion of the patient support assembly, the second actuator for moving the portions of the patient support assembly between the first position and the third position.

6. An apparatus for moving and supporting a patient, comprising;

(a) a base frame, (b) a patient support assembly including an X-ray transparent patient support and an X-ray cartridge carriage behind the X-ray transparent patient support for X-ray imaging of a patient, the X-ray cartridge carrier including a positioning member for movement between an extended position and a retracted position and for movement between an upper position and a lower position, (c) a first actuator coupling the base frame and patient support assembly for moving the patient support assembly between a first substantially horizontal position and a second substantially upright position, the first actuator mounted to the base frame to allow translational movement thereof relative to the base frame thereby causing the patient support assembly to move between the second position and the first position, (d) the patient support assembly having four portions, including: (i) a leg portion, (ii) a linkage frame, (iii) a lower body portion, and (iv) an upper body portion, the leg portion pivotably connected to the linkage frame to rotate relative to the linkage frame about a first axis, the leg portion also pivotably connected to the lower body portion to rotate relative to the lower body portion about a second axis, the upper body portion pivotably connected to the lower body portion to rotate relative to the lower body portion about a third axis, the upper body portion pivotably connected to the linkage frame to rotate relative to the first lower portion about a fourth axis, (e) a second actuator coupling the linkage frame and another portion of the patient support assembly for moving the patient support assembly between a first position for presenting a substantially flat surface for supporting a patient in a supine position and a third position for presenting surfaces that define a chair for supporting a patient in a sitting position.

7. An apparatus for moving and supporting a patient, comprising;

(a) a base frame, (b) a patient support assembly, (c) a first actuator coupling the base frame and patient support assembly for moving the patient support assembly between a first substantially horizontal position a nd a second substantially upright position, the first actuator mounted to the base frame to allow translational movement thereof relative to the base frame thereby causing the patient support assembly to move between the second position and the first position, (d) the patient support assembly having four portions, including: (i) a leg portion, (ii) a linkage frame, (iii) a lower body portion, and (iv) an upper body portion, the leg portion pivotably connected to the linkage frame to rotate relative to the linkage frame about a first axis, the leg portion also pivotably connected to the lower body portion to rotate relative to the lower body portion about a second axis, the upper body portion pivotably connected to the lower body portion to rotate relative to the lower body portion about a third axis, the upper body portion pivotably connected to the linkage frame to rotate relative to the first lower portion about a fourth axis, wherein the portions of the patient support assembly include X-ray transparent patient support panels and wherein the patient support assembly also includes an X-ray carriage for receiving and positioning an X-ray cartridge behind the X-ray transparent patient support panels opposite a patient, the X-ray carriage including transverse tracks fixed to the patient support assembly, transverse rails slidably mounted to the transverse tracks for translation between an extended position and a retracted position, longitudinal tracks fixed to the transverse rails and longitudinal rails slidably mounted to the longitudinal tracks for translation between an upper position and a lower position, the longitudinal rails adapted to slidably receive an X-ray cartridge whereby the X-ray cartridge may be moved between the extended position and the retracted position and positioned between the upper position and the lower position, (e) a second actuator coupling the linkage frame and another portion of the patient support assembly for moving the patient support assembly between a first position for presenting a substantially flat surface for supporting a patient in a supine position and a third position for presenting surfaces that define a chair for supporting a patient in a sitting position.

8. An apparatus for supporting a bariatric patient, comprising;

(a) a base frame, (b) a bariatric patient support assembly pivotably mounted to the base frame for movement between a first substantially horizontal position for supporting a bariatric patient in a supine position and a second substantially upright position for supporting a bariatric patient in a substantially standing position, (c) an actuator connecting the base frame and the bariatric patient support assembly and operable between a retracted position and an extended position for moving the bariatric patient support assembly between the first substantially horizontal position and the second substantially upright position, (d) the bariatric patient support assembly including a lower body portion, a leg portion pivotably mounted at one end of the lower body portion and an upper body portion pivotably mounted at the opposite end of the lower body portion, the portions adjustable between the first substantially horizontal position and a third chair shaped position for supporting a bariatric patient in a seated position, wherein the patient support assembly includes an X-ray transparent patient support and an X-ray cartridge carriage behind the X-ray transparent patient support for X-ray imaging of a patient, the X-ray cartridge carriage including a positioning member for movement between an extended position and a retracted position and for movement between an upper position and a lower position.

* * * * *